(12) United States Patent
Childers

(10) Patent No.: US 8,999,302 B1
(45) Date of Patent: Apr. 7, 2015

(54) SKIN DYE PROTECTANT FORMULATIONS

(75) Inventor: David Alan Childers, Huntington, WV (US)

(73) Assignee: Aplicare, Inc., Meriden, CT (US)

( * ) Notice: Subject to any disclaimer, the term of this patent is extended or adjusted under 35 U.S.C. 154(b) by 569 days.

(21) Appl. No.: 12/603,641

(22) Filed: Oct. 22, 2009

(51) Int. Cl.
| | |
|---|---|
| A61K 31/765 | (2006.01) |
| A61K 47/10 | (2006.01) |
| A61K 9/00 | (2006.01) |
| A61Q 19/00 | (2006.01) |
| A61K 31/192 | (2006.01) |
| A61K 31/047 | (2006.01) |
| A61K 31/355 | (2006.01) |
| A61K 9/70 | (2006.01) |

(52) U.S. Cl.
CPC .............. *A61K 31/765* (2013.01); *A61K 31/192* (2013.01); *A61K 31/047* (2013.01); *A61K 31/355* (2013.01); *A61K 47/10* (2013.01); *A61K 9/0014* (2013.01); *A61K 9/70* (2013.01); *A61K 9/7015* (2013.01); *A61Q 19/00* (2013.01)

(58) Field of Classification Search
None
See application file for complete search history.

(56) References Cited

U.S. PATENT DOCUMENTS

| | | | | |
|---|---|---|---|---|
| 4,820,508 A | * | 4/1989 | Wortzman | 424/59 |
| 4,942,029 A | | 7/1990 | Scheps | |
| 5,242,433 A | * | 9/1993 | Smith et al. | 604/289 |
| 5,747,011 A | * | 5/1998 | Ross et al. | 424/59 |
| 6,146,618 A | | 11/2000 | Bell et al. | |
| 6,165,450 A | * | 12/2000 | Chaudhuri et al. | 424/59 |
| 6,190,645 B1 | * | 2/2001 | SaNogueira et al. | 424/59 |
| 6,414,023 B1 | * | 7/2002 | Brandsborg et al. | 514/546 |
| 6,582,683 B2 | | 6/2003 | Jezior | |
| 6,620,435 B1 | | 9/2003 | Osborne | |
| 6,635,239 B2 | | 10/2003 | Candau | |
| 6,730,645 B1 | | 5/2004 | Foley et al. | |
| 6,762,158 B2 | | 7/2004 | Lukenbach et al. | |
| 7,018,625 B2 | | 3/2006 | Ulmer et al. | |
| 7,381,403 B2 | | 6/2008 | Simonnet | |
| 2003/0133896 A1 | * | 7/2003 | Dietz et al. | 424/70.14 |
| 2004/0180032 A1 | * | 9/2004 | Manelski et al. | 424/70.121 |
| 2005/0191326 A1 | * | 9/2005 | Melker | 424/401 |
| 2008/0181858 A1 | | 7/2008 | Davis et al. | |
| 2009/0068255 A1 | | 3/2009 | Yu et al. | |
| 2009/0074823 A1 | | 3/2009 | Takakura | |
| 2009/0098068 A1 | | 4/2009 | Takakura et al. | |

OTHER PUBLICATIONS

International Cosmetic Ingredient Dictionary and Handbook, seventh edition, vol. 2, pp. 1612-1613 (1997).*

Aitken, et al., An Oxygen Scavenging System for Improvement of Dye Stability in Single-Molecule Fluorescnce Experiments. Biophysical Journal, Mar. 2008, pp. 1826-1835, vol. 94, Biophysical Society, U.S.

Singh, et al., Radiation Protection by the Antioxidant Alpha-Tocopherol Succinate, NATO RTG-099 2005, pp. 16-1-16-10.

(Continued)

*Primary Examiner* — Bethany Barham
*Assistant Examiner* — Barbara Frazier
(74) *Attorney, Agent, or Firm* — Erin Collins

(57) ABSTRACT

Embodiments of a skin dye protectant formulation comprise at least about 30% by weight of a film forming composition, at least about 40% by weight of a solvent, water, at least 0.1% by weight of a dye, and at least about 1% to about 5% of antioxidants, wherein the formulation is operable to substantially maintain the color of the dye when the skin dye protectant formulation is subjected to gamma sterilization.

20 Claims, 1 Drawing Sheet

(56) References Cited

OTHER PUBLICATIONS

Carleton & Agalloco, Validation of Pharmaceutical Processes: Sterile Products, Published by Informa Health Care 1999, pp. 544-547.

Barakat, et al., Radiation Effects on Some Dyes in Non-Aqueous Solvents and in Some Polymeric Films, Radiation Physics & Chemistry, vol. 61, (2001), pp. 129-135, Elsevier Science Ltd, U.S.

* cited by examiner

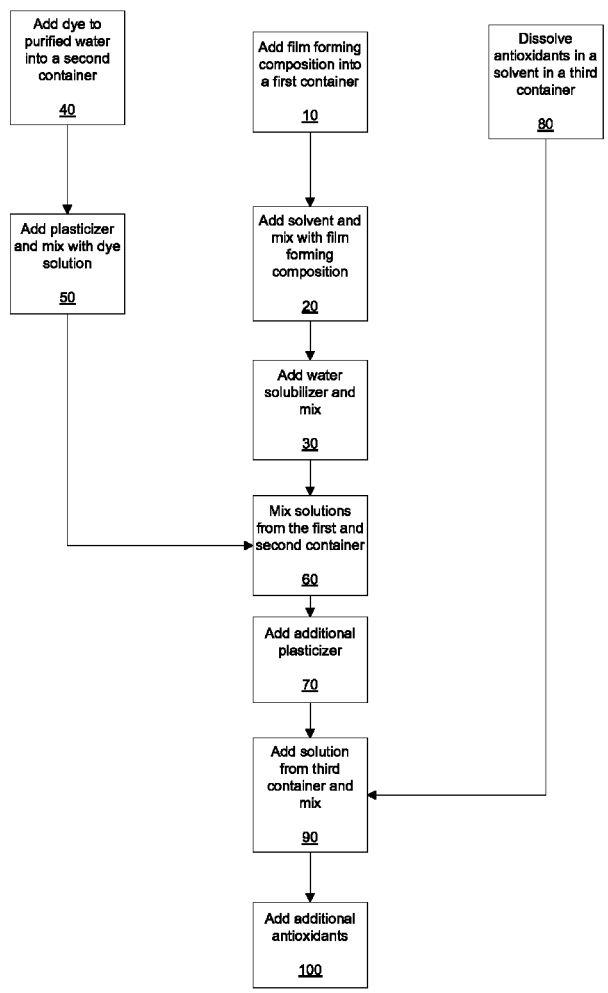

SKIN DYE PROTECTANT FORMULATIONS

TECHNICAL FIELD

Embodiments of the present invention are generally directed to a skin protectant formulation comprising a dye (hereinafter "skin dye protectant formulation"), and are specifically directed to a skin dye protectant formulation operable to resist fading during radiation sterilization.

BACKGROUND

Sterilization methods for medical products are well known for example, the use of ethylene oxide, heat, or radiation. Gamma ray, x-ray or electron beam radiation has been utilized as a preferred means of sterilization. These types of radiation use a high energy beam to kill bacteria, viruses, or other microbial species contained in the packaged medical products, achieving the goal of product sterility. In addition to demands for sterilized medical products, there are also demands dyed or colored absorbable medical devices, which can be easily recognized in bloody surgical fields. However, it has been recognized that radiation sterilization via gamma irradiation causes dye color fading. Consequently, there is a continual need for compositions, specifically compositions utilized in medical products, which are operable to withstand fading during gamma sterilization.

SUMMARY

According to one embodiment, a skin dye protectant formulation is provided. The skin dye protectant formulation comprises at least about 30% by weight of a film forming composition, at least about 40% by weight of a solvent, water, at least 0.1% by weight of a dye, and at least about 1% to about 5% of antioxidants, wherein the formulation is operable to substantially maintain the color of the dye when the skin dye protectant formulation is subjected to gamma sterilization.

According to yet another embodiment, the skin dye protectant formulation comprises at least about 30% by weight of a film forming composition, at least about 40% by weight of a solvent, water, about 1 to about 5% by weight plasticizer, about 0.1 to about 1% by weight water solubilizing component, at least 0.1% by weight of a dye, and at least about 1% to about 5% of antioxidants, wherein the formulation is operable to substantially maintain the color of the dye when the skin dye protectant formulation is subjected to gamma sterilization.

These and additional objects and advantages provided by the embodiments of the present invention will be more fully understood in view of the following detailed description, in conjunction with the drawings.

BRIEF DESCRIPTION OF THE DRAWINGS

The following detailed description of specific embodiments of the present invention can be best understood when read in conjunction with the drawings enclosed herewith.

FIG. 1 is a flow chart describing the method of making the skin dye protectant formulation according to one or more embodiments of the present invention.

The embodiments set forth in the drawings are illustrative in nature and not intended to be limiting of the invention defined by the claims. Moreover, individual features of the drawings and invention will be more fully apparent and understood in view of the detailed description.

DETAILED DESCRIPTION

Embodiments of the present disclosure are directed to skin dye protectant formulations, which may be utilized in medical products. As used herein, skin dye protectant formulations refer to compositions comprising a dye, which may be applied to the skin to form a protective layer, and are operable to resist fading during gamma sterilization. As used herein, medical products may be any storage medium for the skin dye protectant layer, for example, containers, bottles, sheets, packages, boxes, or the like, and may also be any application vehicle, for example, pads, substrates, brushes, swabsticks, or the like. Aplicare manufactures and sells a suitable commercial medical product, Sterile Skin Protectant Prep Pads (for example, product number D010), a skin protectant formulation on a preparation pad, which is used to provide a thin film barrier to protect skin from irritation and provide improved adhesion of a dressing or bandage. It may be used under dressings, adhesive tapes, casts, ostomy appliances, etc.

According to one or more embodiments, the skin dye protectant formulation comprises at least about 30% by weight of a film forming composition, at least about 40% by weight of a solvent, water; at least 0.1% by weight of a dye, and at least about 1% to about 5% of antioxidants, wherein the formulation is operable to substantially maintain the color of the dye when the skin dye protectant formulation is subjected to gamma sterilization. As used herein "gamma sterilization" refers to sterilization of any medical package or device using gamma irradiation at a dose of up to about 125 kGy (kiloGray), or from about 2 to about 50 kGy, or from about 5 to about 40 kGy.

As used herein, "substantially maintain the color" means that the color of the skin dye protectant formulation on the storage medium and/or application vehicle only minimally deteriorates when undergoing gamma sterilization. Further as used herein "minimally deteriorates" means minor fading that still allows an application vehicle to transfer the skin dye protectant formulation onto the skin with the dye intact. If there is too much deterioration of the dye due to gamma sterilization, the dye color cannot be adequately transferred from the application vehicle to the skin. In one specific embodiment, it may be desirable that there is no visible fading of the dye on the application vehicle or storage medium, wherein "visible fading" refers to fading as detectable with the naked eye, but does not rule out some degree of fading as detectable under a microscope.

As stated above, the skin dye protectant formulation comprises a film forming composition, which enables the skin dye protectant formulation to form a film layer that adheres to the skin upon application. This may beneficially provide a clean surface and a barrier to the natural body oils that can affect the adhesion of a dressing or tape. Additionally, the film forming composition may yield a film layer that exhibits a balance of toughness and flexibility. The film forming agent enables the skin dye protectant formulation to be removed intact or substantially intact once a surgical procedure is completed, either with or without the addition of soap and water. The film forming composition may comprise any amount suitable to form a film layer that adheres to the skin upon application. In one or more embodiments, the skin dye protectant formulation may include at least about 30% by weight of a film forming composition, or about 35 to about 45% by weight of the film forming composition.

Many formulations are contemplated for the film forming composition, for example, anionic polymers, nonionic polymers, or mixtures thereof. Examples of nonionic polymers suitable for film deposition are the copolymers of vinyl acetate and crotonic acid, terpolymers of vinyl acetate, crotonic acid and a vinyl ester of an alpha-branched saturated aliphatic monocarboxylic acid such as vinyl neodecanoate, copolymers of methyl vinyl ether and maleic anhydride (molar ratio about 1.1) wherein such copolymers are 50% esterified with a saturated alcohol containing from 1 to 4 carbon atoms such as ethanol or butanol, and acrylic copolymers, terpolymers, etc. containing acrylic acid or methacrylic acid esters of acrylic or methacrylic acid with one or more saturated alcohols having from 1 to 22 carbon atoms such as methyl methacrylate, ethyl acrylate, ethyl methacrylate, n-butyl acrylate, t-butyl acrylate, t-butyl methacrylate, n-butyl methacrylate, n-hexyl acrylate, n-octyl acrylate, lauryl methacrylate and behenyl acrylate, glycols having from 1 to 6 carbon atoms such as hydroxypropyl methacrylate and hydroxyethyl acrylate, styrene, vinyl caprolactam, vinyl acetate, acrylamide, alkyl acrylamides and methacrylamides having 1 to 8 carbon atoms in the alkyl group such as methacrylamide, t-butyl acrylamide and n-octyl acrylamide, and other compatible unsaturated monomers. Further examples of nonionic film forming polymers are homopolymers of N-vinylpyrrolidone and copolymers of N-vinylpyrrolidone with compatible nonionic monomers such as vinyl acetate and terpolymers of ethyl acrylate, butyl methacrylate and methyl methacrylate.

Anionic film forming polymers often are derived from the nonionic types, but include carboxylic acid functions. Alkaline agents are employed to neutralize the carboxylic acid or anhydride transforming them into anionic salts. Examples of suitable neutralizing agents include 2-amino-2-methyl-1,3-propanediol (AMPD); 2-amino-2-ethyl-1,3-propanediol (AEPD); 2-amino-2-methyl-1-propanol (AMP); 2-amino-1-butanol (AB); monoethanolamine (MEA); diethanolamine (DEA); triethanolamine (TEA); monoisopropanolamine (MIPA); diisopropanol-amine (DIPA); triisopropanolamine (TIPA); and dimethyl stearamine (DMS).

In one or more embodiments, the film forming composition comprises a copolymer of methyl vinyl ether and maleic acid, and specifically a monoalkyl ester of the copolymer. In an exemplary embodiment, the film forming agent may comprise Gantrez® ES-435 as produced by ISP Corporation. Gantrez® ES-435 contains about 48 to about 52% Butyl Ester of PVM/MA Copolymer, about 38 to about 52% Isopropyl Alcohol, and less than about 10% Butyl Alcohol The solvent of the skin dye protectant formulation may include any aqueous or non-aqueous solvent that is generally recognized as safe for use in skin care products, including but not limited to water, alcohols, and the like. In one or more embodiments, the solvent may comprise alkyl alcohols and derivatives thereof, isomers of alkyl alcohols and derivatives thereof, and mixtures thereof. In a specific embodiment, the solvent may comprise isopropanol. Various amounts are contemplated herein depending on the solubility of the components used in the formulation. For example, the skin dye protectant formulation may comprise at least 30% solvent, or at least about at least about 40% by weight of a solvent, or about 40 to about 50% by weight of the solvent.

In addition to the solvent, the skin dye protectant formulation may also include water to enhance the solubility of the dye inside the skin dye protectant formulation. The water may comprise purified water, distilled water, tap water, or mixtures thereof. In one exemplary embodiment, the water may comprise purified water. Water may be included in any amount suitable to yield the desired solubility for the dye. The water may be present at an amount of up to 30% by weight, or between 2 and about 20% by weight, or between about 5 and about 10% by weight of the skin dye protectant formulation.

The water may be present in any suitable amount familiar to one of ordinary skill in the art. In one or more embodiments, the dye may comprise at least 0.1% by weight, or about 0.1 to about 0.2% by weight of the dye, or about .15% by weight of the skin dye protectant formulation. Any dye is contemplated herein, specifically any FD&C dye or combinations thereof. A green dye, for example, the Pyla Cert MX-528 green dye produced by Pylam®, is used in exemplary embodiments described below. The dye is preferably added at a level necessary to increase the intensity of the tint to accommodate degradation of the dye without affecting the function of demarking an area on the skin or exceeding the dye solubility.

Antioxidants may also be added to the skin dye protectant formulation to reduce the fading of the dye when the packaged product is gamma sterilized. To achieve this fade resistance, the skin dye protectant formulation may include comprise at least about 1% to about 5% of antioxidants, or about 2% to about 4% by weight of antioxidants.

Various compositions and composition mixtures are contemplated for use as an antioxidant. The antioxidant may be a synthetic or natural antioxidant selected from the group comprising of Vitamin C and derivatives (ascorbic acid); Vitamin E and derivatives (tocopherols, tocotrienols, acetate); eugenol; plant and herbal extracts such as sage extract or rosemary extract; flavonoids and derivatives (including catechins); phenolic acids and derivatives; and 2-tert-butylhydroquinone (TBHQ). The antioxidant may also be selected from the group consisting of butylated hydroxyanisole (BHA); butylated hydroxytoluene; gallates such as octyl gallate, dodecyl gallate, and 3,4,5-trihydroxybenzoic acid n-propyl ester (propyl gallate); 1,2,3-trihydroxybenzene (pyrogallol); gallic acid; fatty acid esters including, but not limited to, methyl esters such as methyl linoleate, methyl oleate, methyl stearate, and other esters such as ascorbic palmitate; disulfuram; tocopherols, such as gamma-tocopherol, delta-tocopherol, alpha-tocopherol alpha-tocopherol acetates; deodorized extract of rosemary; propionate esters and thiopropionate esters such as isopropyl 2-hydroxy-4-methylthio butanoate, lauryl thiodipropionate, or dilauryl thiodipropionate; beta-lactoglobulin; ascorbic acid; amino acids such as phenylalanine, cysteine, tryptophan, methionine, glutamic acid, glutamine, arginine, leucine, tyrosine, lysine, serine, histidine, threonine, asparagine, glycine, aspartic acid, isoleucine, valine, and alanine; 2,2,6,6-tetramethylpiperidinooxy, also referred to as tanan; 2,2,6,6-tetramethyl-4-hydroxypiperidine-1-oxyl, also referred to as tanol; dimethyl-p-phenylaminophenoxysilane; di-p-anisylazoxides; p-hydroxydiphenylamine, and carbonates, phthalates, and adipates thereof; and diludin, a 1,4-dihydropyridine derivative. Moreover, the antioxidant may be selected from the group comprising oil-soluble antioxidants, including, but not limited to ascorbyl palmitate, lecithin, phenyl-alpha-naphthylamine, hydroquinone, and nordihydroguaiaretic acid In one exemplary embodiment, the antioxidants may be selected from the group comprising of Vitamin E and derivatives thereof, rosemary extract and derivatives thereof, ascorbyl palmitate, 2-tert-butylhydroquinone (TBHQ), glyceryl oleate, propylene glycol, vegetable oil, citric acid, and mixtures thereof. One exemplary commercial antioxidant is TENOX 20A® produced Eastman Chemical Company, which is a mixture of TBHQ, glyceryl oleate, propylene glycol, vegetable oil, and citric acid. Rosemary contains a number of potentially biologically active compounds, including antioxidants such as carnosic acid and rosmarinic acid. In one embodiment, the skin dye protectant formulation comprises about 0.8% to about 1% by weight, or about 1% by weight of plant and herbal extracts (e.g., rosemary extract). One such suitable commercial embodiment of the rosemary extract is ProEssential 9120-DN produced by Avatar Corporation.

In the commercial embodiment of the skin dye protectant formulation listed Table 1 below, the 0.1% TBHQ from the Tenox 20A® is at the maximum allowed for topical use. Vitamin E at 0.9% is approaching the maximum amount that can be added without significantly affecting the film properties of the skin dye protectant formulation. Rosemary Extract was increased to the maximum use level of 1% from the 0.1% used in the previous control resulting in 0.04% carnosic acid. The increase in the dye concentration is to increase the intensity of the tint to allow for some degradation of the dye without affecting the function of demarking an area on the skin and without exceeding the dye solubility.

In addition to the above described components of the skin dye protectant formulation, various other additives are contemplated herein. As used herein, the "water solubilizing" agent is an additive used to facilitate the addition of water to the skin dye protectant formulation. Additionally, the water solubilizing agent may be used to keep the near neutral pH and thus provide the lowest potential for skin irritation. In one or more embodiments, the water solubilizing agent may comprise bases such as ammonia and organic amines. These amines may include aminomethyl propanol, or alkanolamines such as, triethylamine, triethanol amine, methyl amine, morpholine, are also contemplated herein. In one embodiment, acids are also contemplated herein, for example, carboxylic acids such as acetic acid, or mineral acids, such as HCl. In one exemplary embodiment, the water solubilizing agent comprises aminomethyl propanol. The aminomethyl propanol may be the commercial product AMP-95™, which is produced by Angus Chemical Company and contains 95% aminomethyl propanol, and 5% water. Aminomethyl propanol is beneficial because it allows the incorporation of the water into the formulation while maintaining adequate water resistance.

The skin dye protectant formulation may comprise any suitable amount to neutralize the water to facilitate the addition of water to the skin dye protectant formulation. The skin dye protectant formulation comprises about 0.1 to about 1% by weight water solubilizing component, or about 0.2 to about 0.5% by weight water solubilizing component.

Additionally, the skin dye protectant formulation may also include a plasticizer, which is a non-volatile component that improves the flexibility of the skin dye protectant formulation to reduce the tendency of the composition to crack. As a result, the plasticizer enables the film to "move with the skin" in products which are applied to skin.

In one or more embodiments, the plasticizer may be selected from the group consisting of glycols, glycol ethers, glycerol esters, acid esters, and mixtures thereof. The glycols may include butylene glycol, propylene glycol, and the like. In one specific embodiment, the plasticizer may comprise propylene glycol. Typically, the acid ester is selected from the group consisting of acetyl tributyl citrate, acetyl triethyl citrate, tributyl citrate, triethyl citrate, acetyl tripropyl citrate, tripropyl citrate, dibutyl sebacate, acetyl dibutyl sebacate, dipropyl sebacate, acetyl dipropyl sebacate, diethyl sebacate, and acetyl diethyl sebacate. Other plasticizers can be used, including homologues and derivatives of these esters. In one exemplary embodiment, the plasticizer is acetyl tributyl citrate. Commercial embodiments of the acetyl tributyl citrate may include the Citroflex® A-4 product manufactured by Vertellus Specialties Inc.

In further embodiment, the plasticizer may comprise multiple components, such acetyl tributyl citrate, and propylene glycol. The propylene glycol aids the addition of the dye solution in addition to acting as a plasticizer. The proportion of propylene glycol to acetyltributyl citrate is adjusted based on the desired film properties. The skin dye protectant formulation may also include any suitable amount operable to adjust the mechanical properties (e.g., the flexibility) of the skin dye protectant formulation. In one embodiment, the skin dye protectant formulation comprises about 1 to about 5% by weight plasticizer.

The following table shows one exemplary composition of the skin dye protectant formulation.

TABLE 1

(Commercial Formulation)

| Ingredient | % by wt of ingredient | Sub-ingredients |
| --- | --- | --- |
| Gantrez ES-435 | 40 | Gantrez ES-435 contains: 48-52% Butyl Ester of PVM/MA Copolymer, 38-52% Isopropyl Alcohol, <10% Butyl Alcohol |
| Isopropyl Alcohol USP | 45.247 | |
| AMP-95 | 0.32 | AMP-95 contains: 95% aminomethyl propanol, and 5% water |
| Propylene Glycol USP | 3.442 | |
| Pyla Cert Green MX-528 dye | 0.150 | |
| Citroflex A-4 | 0.982 | Acetyltributyl citrate |
| Ascorbyl Palmitate NF | 0.6 | |
| dl-alpha tocopherol | 0.9 | |
| Tenox 20-A (TBHQ), | 0.5 | Tenox 20A contains: 32% Canola Oil Glyceride, 30% Zea Mays oil, 20% tert-butylhydroquinone, 15% propylene glycol, and 3% citric acid |
| ProEssential 9120-DN (antioxidant with carnosic acid) | 1.0 | ProEssential 9120-DN is Rosemary Extract from *Rosmarinus officinalis* containing carnosic acid at 4%. |
| Purified Water USP | 6.859 | |
| Total | 100.0 | |

Referring to FIG. 1, an exemplary embodiment for producing the present skin dye protectant formulation. As shown in FIG. 1, a film forming composition (Gantrez ES-435) is added to a first container (step 10). Then, a solvent (Isopropyl Alcohol) is added and mixed with the film forming agent in the first container until the mixture is homogenous (step 20). Next, water solubilizer (aminomethyl propanol (AMP-95)) is added and mixed until the water solubilizer is dissolved (step 30). In some instances, solvent (Isopropyl Alcohol) from step 20 may be added with the water solubilizer (aminomethyl propanol).

In a second container, the dye is dissolved in water (step 40), and then a plasticizer, (propylene glycol USP) is added to the dye and water solution (step 50). It may be desirable that the dye is completely dissolved in water before proceeding. Propylene glycol is added to the dye and water solution to aid the transition of the dye tint from a water solution to a hydro-alcoholic solution. At which point, the mixture of the second container is added to the mixture of the first container (step 60). It is contemplated that additional water may be used to rinse the remaining dye from the second container for addition to the first container. Subsequently, a second plasticizer (acetyl tributyl citrate (Citroflex A-4)) is added to the first container (step 70).

In a third container, antioxidants (Ascorbyl Palmitate NF and DL-alpha tocopherol) are dissolved in a solvent (Isopropyl Alcohol) (step 80). Next, the mixture of the third container is added to the mixture of the first container (step 90). Next, additional antioxidants (Tenox-20A and ProEssential 9120-DN) are added until the mixture is made homogeneous. Additionally, solvent may also be used during addition of plasticizer (step 70) to rinse the Citroflex (plasticizer) of step 7 and the antioxidant addition steps 80 and 100, at which point the exemplary skin dye protectant formulation is produced.

It is further noted that terms like "preferably," "generally," "commonly," "desirably", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is additionally noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention. While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A skin dye protectant formulation consisting of:
   about 30% to about 45% by weight of a film forming composition;
   about 40% to about 50% by weight of a solvent selected from the group consisting of: alkyl alcohols and derivatives thereof, isomers of alkyl alcohols and derivatives thereof and mixtures thereof;
   about 2% to about 20% by weight of water;
   about 0.1% to about 0.2% by weight of a dye which dissolves in water;
   about 1% to about 5% by weight of antioxidants
   optionally, a plasticizer; and
   optionally, a water solubilizing agent;
   wherein the formulation substantially maintains the color of the dye, when the skin dye protectant formulation subjected to gamma sterilization.

2. The skin dye protectant formulation of claim 1 wherein the film forming composition comprises a copolymer of methyl vinyl ether and maleic acid.

3. The skin dye protectant formulation of claim 1 wherein the film forming composition is a monoalkyl ester of a methyl vinyl ether and maleic acid copolymer.

4. The skin dye protectant formulation of claim 1 wherein the skin dye protectant formulation comprises 35% to about 45% by weight of the film forming composition.

5. The skin dye protectant formulation of claim 1 wherein the dye is substantially green.

6. The skin dye protectant formulation of claim 1 wherein the solvent comprises isopropanol.

7. The skin dye protectant formulation of claim 1 wherein the solvent is an alkyl alcohol.

8. The skin dye protectant formulation of claim 1 wherein the skin dye protectant formulation further comprises about 0.1% to about 1% by weight of water solubilizing component.

9. The skin dye protectant formulation of claim 8 wherein the water solubilizing component comprises at least one alkanolamine.

10. The skin dye protectant formulation of claim 8 wherein the water solubilizing component comprises aminomethyl propanol.

11. The skin dye protectant formulation of claim 1 wherein the skin dye protectant formulation has a substantially neutral pH.

12. The skin dye protectant formulation of claim 1 wherein the skin dye protectant formulation further comprises about 1% to about 5% by weight of plasticizer.

13. The skin dye protectant formulation of claim 12 wherein the plasticizer is selected from the group consisting of glycols, glycol ethers, glycerol esters, acid esters, and mixtures thereof.

14. The skin dye protectant formulation of claim 13 wherein the acid ester comprises acetyl tributyl citrate and glycol comprises propylene glycol.

15. The skin dye protectant formulation of claim 1 wherein the skin dye protectant formulation comprises about 2% to about 4% by weight of antioxidants.

16. The skin dye protectant formulation of claim 1 wherein the antioxidants comprise plant and herbal extracts.

17. The skin dye protectant formulation of claim 1 wherein the antioxidants are selected from the group consisting of: Vitamin E, rosemary extract, ascorbyl palmitate, 2-tert-butyldroquinone (TBHQ), glyceryl oleate, propylene glycol, vegetable oil, citric acid and mixtures thereof.

18. A skin dye protectant formulation consisting of:
   a film forming composition;
   about 40% to about 50% by weight of a solvent selected from the group consisting of: alkyl alcohols, isomers of alkyl alcohols and mixtures thereof;
   about 2% to about 20% by weight of water;
   about 0.1% to about 0.2% by weight of a dye which dissolves in water;
   about 1% to about 5% by weight of antioxidants, and
   about 1% to about 5% of a plasticizer; and
   optionally, a water solubilizing agent;
   wherein the color of the dye is maintained when the skin dye protectant formulation is subjected to gamma sterilization.

19. A skin dye protectant formulation consisting of:
   about 30% to about 45% by weight of a film forming composition;

about 40% to about 50% by weight of a solvent selected from the group consisting of: alkyl alcohols, isomers of alkyl alcohols and mixtures thereof;

about 1% to about 5% by weight of a plasticizer;

about 0.1% to about 1% by weight of a dye which dissolves in water;

about 1% to about 5% of antioxidants; and a water solubilizing agent.

20. The skin dye protectant formulation of claim 18 further comprising about 0.1% to about 1% by weight water solubilizing component.

* * * * *